US012343352B2

(12) United States Patent
Zhai et al.

(10) Patent No.: US 12,343,352 B2
(45) Date of Patent: Jul. 1, 2025

(54) N-(PHENYLSULFONYL)BENZAMIDES AND RELATED COMPOUNDS AS Bcl-2 INHIBITORS

(71) Applicants: ASCENTAGE PHARMA (SUZHOU) CO., LTD., Suzhou (CN); ASCENTAGE PHARMA GROUP CORP LIMITED, Hong Kong (CN)

(72) Inventors: Yifan Zhai, Suzhou (CN); Dajun Yang, Suzhou (CN); Zi Chen, Suzhou (CN)

(73) Assignees: ASCENTAGE PHARMA (SUZHOU) CO., LTD., Jiangsu (CN); ASCENTAGE PHARMA GROUP CORP LIMITED, Hong Kong (CN)

(*) Notice: Subject to any disclaimer, the term of this patent is extended or adjusted under 35 U.S.C. 154(b) by 127 days.

(21) Appl. No.: 17/287,661

(22) PCT Filed: Dec. 3, 2020

(86) PCT No.: PCT/CN2020/133621
§ 371 (c)(1),
(2) Date: Apr. 22, 2021

(87) PCT Pub. No.: WO2021/110097
PCT Pub. Date: Jun. 10, 2021

(65) Prior Publication Data
US 2022/0305034 A1 Sep. 29, 2022

(30) Foreign Application Priority Data

| Dec. 3, 2019 | (WO) | PCT/CN2019/122608 |
| Mar. 9, 2020 | (WO) | PCT/CN2020/078364 |
| Jun. 12, 2020 | (WO) | PCT/CN2020/095844 |
| Jul. 8, 2020 | (WO) | PCT/CN2020/100903 |
| Nov. 27, 2020 | (CN) | 202011352984.1 |

(51) Int. Cl.
| A61K 31/635 | (2006.01) |
| A61K 31/454 | (2006.01) |
| A61K 31/4745 | (2006.01) |
| A61K 31/519 | (2006.01) |
| A61K 31/55 | (2006.01) |
| A61K 31/573 | (2006.01) |
| A61K 31/706 | (2006.01) |
| A61K 39/395 | (2006.01) |
| A61P 35/02 | (2006.01) |

(52) U.S. Cl.
CPC .......... *A61K 31/635* (2013.01); *A61K 31/454* (2013.01); *A61K 31/4745* (2013.01); *A61K 31/519* (2013.01); *A61K 31/55* (2013.01); *A61K 31/573* (2013.01); *A61K 31/706* (2013.01); *A61K 39/3955* (2013.01); *A61P 35/02* (2018.01)

(58) Field of Classification Search
CPC .............................. A61K 31/635; A61P 35/00
See application file for complete search history.

(56) References Cited

U.S. PATENT DOCUMENTS

| 2017/0209462 A1 | 7/2017 | Bilotti et al. |
| 2018/0250298 A1 | 9/2018 | Hamdy et al. |
| 2018/0354950 A1* | 12/2018 | Wang .................. C07D 471/04 |
| 2023/0398115 A1 | 12/2023 | Caponigro et al. |

FOREIGN PATENT DOCUMENTS

| CN | 108135904 | 6/2018 |
| CN | 108348520 | 7/2018 |
| CN | 109311871 | 2/2019 |
| TW | 201618772 A | 6/2016 |
| WO | 2017/040617 A1 | 3/2017 |
| WO | 2017037579 A1 | 3/2017 |
| WO | 2018027097 A1 | 2/2018 |
| WO | 2020024820 A1 | 2/2020 |
| WO | 2020024826 A1 | 2/2020 |
| WO | 2020024834 A1 | 2/2020 |
| WO | 2020024916 A1 | 2/2020 |
| WO | 2020103921 A1 | 5/2020 |
| WO | 2021/110136 A1 | 6/2021 |

OTHER PUBLICATIONS

"Pharmacokinetics & Pharmacodynamics: Dose Selection & the Time Course of Drug Action" by Holford et al., Chapter 3 in Basic & Clinical Pharmacology, 7th Ed., Katzung (Ed.), Appleton & Lange (Stamford, Connecticut), copyright 1989, pp. 34-49. (Year: 1989).*

Hanaizi et al., "The European medicines agency review of pomalidomide in combination with low-dose dexamethasone . . . ," Oncologist 2015;20(3):329-34. PMID: 25673103. (Year: 2015).*

Sun, Mingyuan, et al. "A Phase 1 study to evaluate the safety, pharmacokinetics (PK) and pharmacodynamics (PD) of isaftoclax (APG-2575), a novel BCL-2 inhibitor (BCL-2i), in patients (pts) with certain relapsed or refractory (R/R) hematologic malignancies (HMs)." Blood, 2021, p. 3730-3732, vol. 138.

ASCO 2022 I Ascentage Pharma Releases Updated Data Demonstrating Lisaftoclax-s (APG-2575) Therapeutic Potential in Patients with R/R CLL/SLL, News Provided By Ascentage Pharma—Jun. 7, 2022.

Marina Konopleva et al., "Efficacy and Biological Correlates of Response in a Phase II Study of Venetoclax Monotherapy in Patients with Acute Myelogenous Leukemia," Cancer Discovery, Aug. 12, 2016, pp. 1106-1117, vol. 6, No. 10, American Association for Cancer Research, Philadelphia, PA, USA.

Extended European Search Report for European Patent Application No. 20895135.0-1112 / 3914251, dated Feb. 21, 2022, 4 pages.

Taiwan Office Action for 11020877800, dated Sep. 7, 2021 with English Translation.

Taiwan Search Report for 11020877800, dated Sep. 7, 2021.

ISR for International Application No. PCT/CN2020/133621, dated Mar. 3, 2021 (Ascentage Pharma (Suzhou) Co., LTD., et al.

(Continued)

*Primary Examiner* — Theodore R. Howell
(74) *Attorney, Agent, or Firm* — Barnes & Thornburg LLP (57) ABSTRACT

Described herein are methods of treating a hematologic malignancy in a patient in need thereof, comprising administering to the patient a Bcl-2 inhibitor in a step-wise dosing regimen.

12 Claims, 4 Drawing Sheets

(56) References Cited

OTHER PUBLICATIONS

Leung N, ThoméSD, et al. "Venetoclax induced a complete response in a patient with immunoglobulin light chain amyloidosis plateaued on cyclophosphamide, bortezomib and dexamethasone". Haematologica, Mar. 2018., pp. e135-e137, vol. 103, No. 3.
Clinical Trials.gov ID NCT 03537482-v5, "APG-2575 Study of Safety, Tolerability, PK/PD in Patients With Hematologic Malignancies", https://www.clinicaltrials.gov/study/NCT03537482, appendix pp. 1-6, Publication date Feb. 15, 2019.
Clinical Trials.gov ID NCT03913949-v2, "A Study to Evaluate the Safety,PK and PD of APG-2575 in Patients With Hematologic Malignancies", https://www.clinicaltrials.gov/study/NCT03913949, appendix pp. 1-6, Publication date Jun. 26, 2019.
Roeker, Lindsey E., et al. "Tumor lysis, adverse events, and dose adjustments in 297 venetoclax-treated CLL patients in routine clinical practice." Clinical Cancer Research 25.14 (2019): 4264-4270. (7 pages).
CAS Registry No. 2180923-05-09, entered Feb. 27, 2018 (1 page).
"Advanced Tutorial on Nephrology", edited by Chen Xiangmei, People's Military Medical Press, 1st edition, pp. 211-212, section 3, Publication Date Sep. 30, 2014 (6 pages).
"Practical Clinical Diagnosis and Treatment of Cancer Diseases", edited by Yang Chunmei, et al., Jilin Science and Technology Shu Publishing House, 1st edition, p. 471, section 3, Publication Date Mar. 31, 2018 (5 pages).
Chinese Office Action issued in CN Application No. 202011411048.3 on Apr. 19, 2024 (23 pages).
Ailawadhi, Sikander, et al., "Novel BCL-2 Inhibitor Lisaftoclax in Relapsed or Refractory Chronic Lymphocyctic Leukemia and Other Hematologic Malignancies: First-in-Human Open-Label Trial," Clinical Cancer Research, Clinical Trials: Targeted Therapy, AACRJournals.org, 2385, 21 pages.
Acsentage Pharma "Ascentage Pharma's Bcl-2 Inhibitor Lisaftoclax in Combinations Demonstrates Potential Clinical Benefit in Patients with Prior Exposure to Venetoclax," Live from ASH 2024, Oral Report, Dec. 10, 2024, 8 pages.
Acsentage Pharma "Oral Report Features Encouraging Data of Ascentage Pharma's Bcl-2 Inhibitor Lisaftoclax in R/R MM, Including a Median PFS Over 9 Months," Live from ASH 2024, Oral Report, Dec. 10, 2024, 8 pages.
Acsentage Pharma "Ascentage Pharma Releases Updated Data of Bcl-2 Inhibitor Lisaftoclax in MDS that Demonstrates Potential Clinical Benefits and Favorable Safety," Live from ASH 2024, Oral Report, Dec. 10, 2024, 8 pages.

* cited by examiner

FIG. 5a. Part One study Design

FIG. 5b. Part Two study Design

MTD/RP2D^A: MTD/RP2D of Arm A

MTD/RP2D^B: MTD/RP2D of Arm B

N-(PHENYLSULFONYL)BENZAMIDES AND RELATED COMPOUNDS AS Bcl-2 INHIBITORS

CROSS REFERENCE TO RELATED APPLICATIONS

This application is a national phase of International Patent Application No. PCT/CN2020/133621, filed Dec. 3, 2020, which claims priority to Chinese Patent Application No. 202011352984.1, filed Nov. 27, 2020, and to International Patent Application No. PCT/CN2020/100903, filed Jul. 8, 2020, to International Patent Application No. PCT/CN2020/095844, filed Jun. 12, 2020, to International Patent Application No. PCT/CN2020/078364 filed Mar. 9, 2020, and PCT/CN2019/122608, filed Dec. 3, 2019, all of which are incorporated by reference herein in their entirety.

BACKGROUND

Apoptosis, the process of programmed cell death, is an essential biological process for tissue homeostasis. In mammals, it has been shown to regulate early embryonic development. Later in life, cell death is a default mechanism by which potentially dangerous cells, e.g., cells carrying cancerous defects, are removed. Several apoptotic pathways are known. One of the most important apoptotic pathways involves the Bcl-2 family of proteins which are key regulators of the mitochondrial (also called "intrinsic") pathway of apoptosis. The structural homology domains BH1, BH2, BH3 and BH4 are characteristic of Bcl-2 family proteins. The Bcl-2 family of proteins can be further classified into three subfamilies depending on how many of the homology domains each protein contains and on its biological activity, i.e., whether it has pro- or anti-apoptotic function.

Down-regulated apoptosis (and more particularly the Bcl-2 family of proteins) may be involved in the onset of cancerous malignancy. The anti-apoptotic proteins, Bcl-2 and Bcl-xL, are over-expressed in many cancer cell types. The effect of this deregulation is the survival of altered cells which would otherwise have undergone apoptosis in normal conditions. The repetition of these defects associated with unregulated proliferation is thought to be the starting point of cancerous evolution. Additionally, BH3-only proteins can act as tumor suppressors when expressed in diseased animals.

The natural expression levels of anti-apoptotic Bcl-2 family proteins members vary in different cell types. For example, in young platelets, Bcl-xL protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal, i.e., non-cancerous, cells, and the recognized inter-cell type variability of Bcl-2 family protein expression, it is advantageous to have a small molecule inhibitor that selectively targets and preferably binds to one type or a subset of anti-apoptotic Bcl-2 protein(s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others, e.g., lymphopenia has been observed in Bcl-2 deficient mice.

There is an ongoing need for compounds that selectively inhibit the activity of one type or a subset of Bcl-2 proteins for the treatment of hyperproliferative diseases such as cancer, including hematologic malignancies.

SUMMARY

The present disclosure provides, for example, methods of treating a hematologic malignancy in a patient in need thereof, comprising administering to the patient a Bcl-2 inhibitor in a step-wise dosing regimen.

For example, described herein, in part, is a method of treating a hematologic malignancy in a patient in need thereof, comprising: administering a daily step-wise dosing regimen of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt thereof; wherein administering the daily step-wise dosing regimen comprises: administering a first dose of 20 mg of the compound to the patient for one day; administering a second dose of 50 mg of the compound to the patient for one day, on the day after the first dose, and administering a third dose of 100 mg of the compound to the patient for one day, on the day after the second dose.

In another embodiment, described herein is a method of treating a hematologic malignancy in a patient in need thereof, comprising: administering a daily step-wise dosing regimen of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt thereof; wherein administering the daily step-wise dosing regimen comprises administering a first dose of 20 mg to 100 mg of the compound to the patient for one day; administering a second dose of 50 mg to 200 mg of the compound to the patient for one day, on the day after the first dose.

In another embodiment, also described herein is a method of treating a hematologic malignancy in a patient in need thereof, wherein the patient is also being administered a CYP2C8 inhibitor, another CYP inhibitor (such as CYP3A4 inhibitor) or certain foods such as grapefruit juice, comprising administering an effective amount of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt to the patient, wherein the effective amount for the patient taking the CYP2C8 inhibitor is about 60% or less, about 50% or less, about 40% or less, or about 20% or less, than an effective amount for a patient who is not being administered a CYP2C8 inhibitor.

BRIEF DESCRIPTION OF THE DRAWINGS

FIG. 5 depicts a study design for an exemplary Phase Ib/II Study of Compound 1 as a Single Agent or in Combination with ibrutinib or rituximab in patients with relapsed and/or refractory chronic Lymphocytic leukemia (CLL) or relapsed and/or refractory small Lymphocytic Lymphoma (SLL). The study comprises (a) a dose expansion study using Compound 1 as a single agent to in order to evaluate the safety and antitumor activity and pharmacokinetic profile of Compound 1 monotherapy in patients with relapsed or refractory CLL/SLL (FIG. 5a) and (b) a study of Compound 1 in combination with ibrutinib or rituximab to explore the dose-limiting toxicity (DLT), maximum tolerated dose (MTD), Phase II recommended dose (RP2D), and safety of Compound 1 in the studied combination therapy regimens, as well as pharmacokinetic studies and efficacy evaluation (FIG. 5b).

DETAILED DESCRIPTION

As described herein, the compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide has the structure:

"Compound 1" as described herein refers to (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, which has the structure:

As described herein, the compound (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide has the structure:

"Compound Z" refers to a compound of the structure:

Compound Z is also known as Venetoclax.

Compounds used in the methods described herein, such as N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, and (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, are contemplated as having better efficacy than other known Bcl-2 inhibitors, e.g., Venetoclax (Compound Z), in patients based on a combination of antiproliferative, antitumor, and apoptosis induction activities exhibited by Compound 1. Additionally, Compound 1 exhibits preferable pharmacokinetic properties than Compound Z, such as shorter half-life and higher $C_{max}$ in systemic exposure in combination with similar half-life and higher $C_{max}$ in tumor tissues. Such preferable pharmacokinetic properties can result in lower toxicity without affecting the therapeutic efficacy of the compound.

The methods described herein can reduce the risk of a patient developing tumor lysis syndrome (TLS) during treatment for a hematologic malignancy. TLS is a common yet dangerous side-effect that can be experienced by patients during administration of a Bcl-2 inhibitor. To reduce the risk of TLS, weekly ramp-up regimens that lead up to the recommended therapeutic dose are utilized in patients administered the Bcl-2 inhibitor Venetoclax. However, such a weekly ramp-up dosing regimen can result in low drug exposure and negatively impact the efficacy of the Bcl-2 inhibitor. The methods described herein comprise a more therapeutically efficacious daily ramp-up dosing regimen that allows for a shorter time needed to achieve the standard therapeutic dose of the compound administered while contemporaneously reducing the risk of TLS.

Methods of Use

In one embodiment, described herein is a method of treating a hematologic malignancy in a patient in need thereof, comprising: administering a daily step-wise dosing regimen of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt thereof; wherein administering the daily step-wise dosing regimen comprises: administering a first dose of 20 mg of the compound to the patient for one day; administering a second dose of 50 mg of the compound to the patient for one day, on the day after the first dose, and administering a third dose of 100 mg of the compound to the patient for one day, on the day after the second dose. In some embodiments, the method further comprises administering to the patient a fourth dose of 200 mg of the compound daily for 1 to 5 days or more. In some embodiments, the fourth dose is administered to the patient for one day. In some embodiments, the daily step-wise regimen further comprises administering to the patient a fifth dose of 400 mg after the fourth dose is administered. In some embodiments, the method further comprises administering to the patient a dose of 400 mg to 800 mg of the compound daily, after the third or fourth dose. In some embodiments, the method further comprises administering to the patient a daily dose of 400 mg, 600 mg or 800 mg of the compound for 1 week or more, or 1 month or more, after administering the daily step-wise dosing regimen. In some embodiments, the method further comprises administering to the patient a daily dose of 400 mg, 600 mg, 800 mg, or 1000 mg of the compound for 1 week or more, or 1 month or more, after administering the daily step-wise dosing regimen. In some embodiments, the compound is (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide. In some embodiments, the compound is (S)-N-((4-(((1,4-dioxan-2-yl)methyl)amino)-3-nitrophenyl)sulfonyl)-2-((1H- pyrrolo[2,3-b]pyridin-5-yl)oxy)-4-(4-((6-(4-chlorophenyl)spiro[3.5]non-6-en-7-yl)methyl)piperazin-1-yl)benzamide.

Also contemplated herein is a method of treating a hematologic malignancy and/or Immunoglobulin Light Chain Amyloidosis in a patient in need thereof, comprising: administering a daily step-wise dosing regimen of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt thereof; wherein administering the daily step-wise dosing regimen comprises administering a first dose of 20 mg to 100 mg of the compound to the patient for one day; administering a second dose of 50 mg to 200 mg of the compound to the patient for one day, on the day after the first dose. In some embodiments, the daily step-wise dosing regimen comprises administering a first dose of 100 mg of the compound to the patient for one day. In some embodiments, the daily step-wise dosing regimen further comprises administering a third dose of 100 to 400 mg of the compound to the patient for one day, on the day after the second dose. In some embodiments, the daily step-wise dosing regimen further comprises administering a fourth dose of 200 mg to 800 mg of the compound to the patient for one to seven days after the third dose. In some embodiments, the method further comprises administering to the patient, after the daily step-wise dosing regimen, about 400 mg to 800 mg of the compound daily for 1 week or more. In some embodiments, the method further comprises administering to the patient, after the daily step-wise dosing regimen, about 400 mg to 1000 mg of the compound daily for 1 week or more. In some embodiments, the patient, during or after administration of the daily step-wise dosing regimen, has a reduced risk of tumor lysis syndrome. In some embodiments, the hematologic malignancy is selected from the group consisting of chronic lymphocytic leukemia, acute myeloid leukemia, multiple myeloma, lymphoplasmacytic lymphoma, non-Hodgkin's lymphoma, and small lymphocytic leukemia, Immunoglobulin Light Chain Amyloidosis. In some embodiments, the hematologic malignancy is selected from the group consisting of chronic lymphocytic leukemia, acute myeloid leukemia, multiple myeloma, lymphoplasmacytic lymphoma, and non-Hodgkin's lymphoma. In some embodiments, the hematologic malignancy is selected from chronic lymphocytic leukemia and small lymphocytic leukemia. In some embodiments, the hematologic malignancy is Waldenström Macroglobulinemia. In some embodiments, the patient has primary refractory acute myeloid leukemia. In some embodiments, the patient has refractory small lymphocytic leukemia or refractory chronic lymphocytic leukemia. In some embodiments, the patient has relapsed after a previous hematologic malignancy therapy. In some embodiments, the previous hematologic malignancy therapy is a therapy for chronic lymphocytic leukemia In some embodiments, the previous hematologic malignancy therapy is a therapy for small lymphocytic leukemia. In some embodiments, the previous hematologic malignancy therapy is a therapy for acute myeloid leukemia. In some embodiments, the patient has received at least one prior therapy for the hematologic malignancy, e.g., the patient has previously been administered ibrutinib, obinutuzumab, bendamustine, prednisone, fludarabine, cyclophosphamide, pentostatin, or a combination of two or more thereof; and/or the patient has previously had radiation or surgical therapy. In some embodiments, the method further comprises administering rituximab to the patient before, during or after the daily step-wise dosing regimen. In some embodiments, the method further comprises administering rituximab to the patient after the daily step-wise dosing regimen. In some embodiments, the rituximab is administered to the patient about 1 week or more after the daily step-wise dosing regimen. In some embodiments, the method further comprises administering azacytidine, decitabine or low-dose cytarabine to the patient before, during or after the daily step-wise dosing regimen. In some embodiments, the method further comprises administering ibrutinib, topetecan, an MDM2 inhibitor, a CD20 inhibitor, a CDK9i inhibitor, or Homoharringtonine (HTT) inhibitor to the patient before, during or after the daily step-wise dosing regimen. In some embodiments, the method further comprises administering ibrutinib, topetecan, an MDM2 inhibitor, a CD20 inhibitor, a CDK9i inhibitor, or Homoharringtonine (HTT) inhibitor to the patient after the daily step-wise dosing regimen. In some embodiments, the method further comprises administering a BTK inhibitor to the patient before, during or after the daily step-wise dosing regimen. In some embodiments, the method further comprises administering a BTK inhibitor to the patient after the daily step-wise dosing regimen. In some embodiments, the BTK inhibitor is administered to the patient about 1 week or more after the daily step-wise dosing regimen. In some embodiments, the BTK inhibitor is ibrutinib. In some embodiments, the method further comprises administering azacytidine to the patient before, during or after the daily step-wise dosing regimen. In some embodiments, the method further comprises administering azacytidine to the patient after the daily step-wise dosing regimen. In some embodiments, the method further comprises administering homoharringtonine to the patient before, during or after the daily step-wise dosing regimen. In some embodiments, the method further comprises comprising administering homoharringtonine to the patient after the daily step-wise dosing regimen. In some embodiments, the compound is (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide. In some embodiments, the compound is (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide.

In another embodiment, provided herein method of treating multiple myeloma and/or Immunoglobulin Light Chain Amyloidosis in a patient in need thereof, comprising: administering to the patient 200 mg or more of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt thereof. In some embodiments, the method further comprises administering pomalidomide and dexamethasone to the patient. In some embodiments, the method further comprises administering lenalidomide and dexamethasone to the patient. In some embodiments, the method further comprises administering daratumumab, lenalidomide, and dexamethasone to the patient. In some embodiments, the method comprises administering 200 mg, 400 mg, 600 mg, or 800 mg of the compound to the patient. In some embodiments, the patient has refractory multiple myeloma. In some embodiments, the patient has relapsed after a previous therapy for multiple myeloma. In some embodiments, the compound is (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide. In some embodiments, the compound is (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide.

In another embodiment, described herein is a method of treating a hematologic malignancy in a patient in need thereof, wherein the patient is also being administered a CYP2C8 inhibitor (and/or another drug that may cause a drug/drug interaction, such as a CYP3A4 inhibitor, or a food such as grapefruit juice), comprising administering an effective amount of a compound N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide or a pharmaceutically acceptable salt to the patient, wherein the effective amount for the patient taking the CYP2C8 inhibitor is about 60% or less, about 50% or less, about 40% or less, or about 20% or less, than an effective amount for a patient who is not being administered a CYP2C8 inhibitor (or, in certain embodiments other drugs or foods such as grapefruit juice, or a CYP3A4 inhibitor). In some embodiments, the effective amount for the patient taking the CYP2C8 inhibitor is about 20 mg to about 100 mg daily of the compound. In some embodiments, the effective amount for the patient taking the CYP2C8 inhibitor is about 10 mg, 20 mg, 30 mg, 40 mg, 50 mg, 100 mg or 200 mg per day. In some embodiments, the method comprises administering the effective amount for the patient taking the CYP2C8 inhibitor after administering the compound by an initial daily or weekly step-wise dosing regimen. In some embodiments, the CYP2C8 inhibitor is a strong CYP2C8 inhibitor. In some embodiments, the CYP2C8 inhibitor is selected from the group consisting of gemfibrozil, trimethoprim, thiazolidediones, montelukast, and quercetin. In some embodiments, the compound is (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide. In some embodiments, the compound is (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide.

Definitions

An "effective amount" includes the amount of the subject compound that will elicit the biological or medical response of a tissue, system, animal or human that is being sought by the researcher, veterinarian, medical doctor or other clinician. A compound described herein, e.g., Compound 1, is administered in effective amounts to treat a condition, e.g., a hematologic malignancy. Alternatively, an effective amount of a compound is the quantity required to achieve a desired therapeutic and/or prophylactic effect, such as an amount which results in the prevention of or a decrease in the symptoms associated with the condition.

"Individual," "patient," or "subject" are used interchangeably herein and include any animal, including mammals, including mice, rats, other rodents, rabbits, dogs, cats, swine, cattle, sheep, horses, or primates, and humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods described herein is desirably a mammal in which treatment of a disorder described herein is desired, such as a human.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, "treating" includes any effect, e.g., lessening, reducing, modulating, or eliminating, that results in the improvement of the condition, disease, disorder and the like.

A compound described herein, e.g., Compound 1 or pharmaceutically acceptable salt thereof, can be formulated as a pharmaceutical composition using a pharmaceutically acceptable carrier and administered by a variety of routes. In some embodiments, such compositions are for oral administration. In some embodiments, such compositions are for parenteral (by injection) administration. In some embodiments, such compositions are for transdermal administration. In some embodiments, such compositions are for intravenous (IV) administration. In some embodiments, such compositions are for intramuscular (IM) administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995).

EXAMPLES

The compounds described herein can be prepared in a number of ways based on the teachings contained herein and synthetic procedures known in the art. It is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, and Compound 1 can be synthesized in accordance with the synthetic methods described in WO 2018/027097, which is incorporated herein by reference.

Abbreviations: PK: pharmacokinetics; MTD: maximum tolerated dose; DLT: dose-limiting toxicity; RP2D: Recommended Phase 2 Dose; BTKi: BTK inhibitor.

Example 1. Clinical Study of Hematologic Malignancies in Human Patients

Compound 1 is evaluated in a dose-escalation phase of a Phase 1 study for treating patients with a hematologic malignancy. In the study, a 3+3 dose escalation cohort is dosed at a ramp-up schedule consisting of increasing doses of Compound 1 or placebo on a daily basis until a recommended daily dose is achieved. Dosing will begin at 20 mg. Subsequent dosing increments per day are 50 mg, 100 mg, 200 mg, 400 mg, 600 mg and 800 mg based on the which recommended daily dose is set for the cohort.

From this dosing scheme, dose escalation occurs until a maximum tolerated dose (MTD) will be determined. The MTD is the recommended daily dose in a dose expansion cohort of a maximum of 20 patients in which the daily ramp-up schedule as described above is applied until the MTD is achieved.

Figure 1:
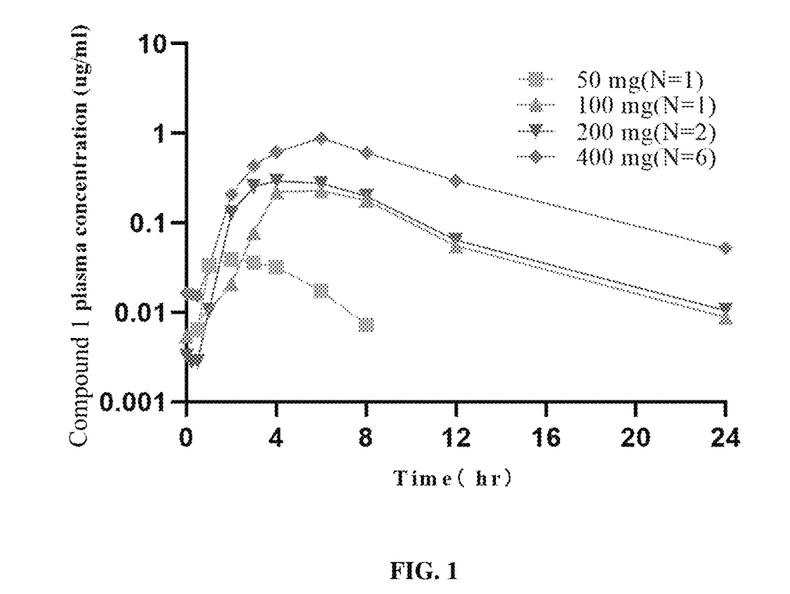
FIG. 1 depicts exemplary plasma concentration-time profiles of Compound Z following a single oral administration of 50 mg, 100 mg, 200 mg, and 400 mg in human patients.
Figure 2:
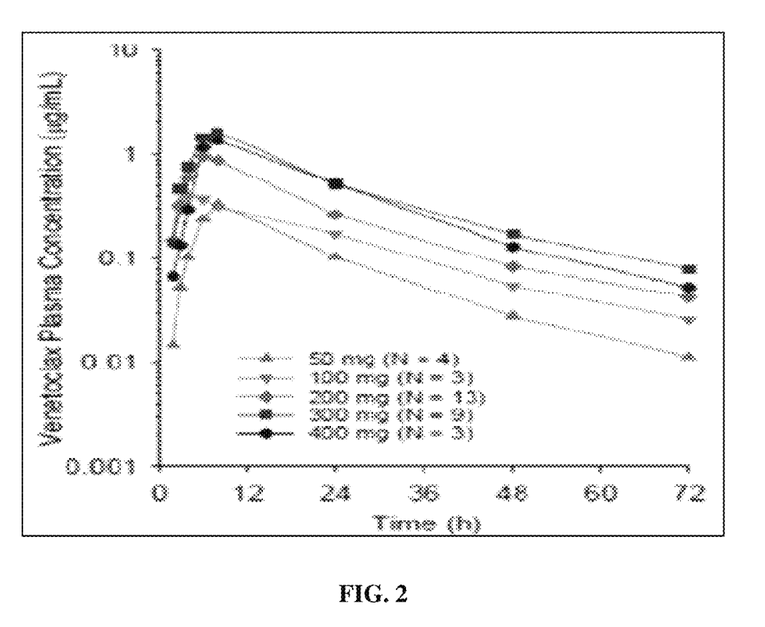
FIG. 2 depicts exemplary plasma concentration-time profiles of Compound Z following a single oral administration of 50 mg, 100 mg, 200 mg, 300 mg, and 400 mg in human patients.

Example 2. Clinical Pharmacology of Compound 1 and Compound Z in Human Patients Pharmacokinetics of Compound 1 and Compound Z were evaluated in patients. For example, plasma concentration-time profiles of Compound 1 and Compound Z following a single oral administration of 50 mg, 100 mg, 200 mg, 300 mg (Compound Z only), and 400 mg in patients are shown in FIG. 1 and FIG. 2, respectively.

Further, Table 1 shows comparisons of pharmacokinetic parameters at steady state between Compound 1 and Compound Z following multiple oral doses of 400 mg once daily.

TABLE 1

Comparisons of Steady State Pharmacokinetics between Compound 1 and Compound Z Following Multiple Oral Doses of 400 mg Once Daily.

|  | N | $T_{max}$ (h) | $C_{max}$ (μg/mL) | AUC(0-24 h) (μg * h/mL) | $T\frac{1}{2}$ (h) |
| --- | --- | --- | --- | --- | --- |
| Compound 1 | 4 | 6 (6–8) | 0.970 (45%) | 9.96 (32%) | 4.43 (9%) |
| Compound Z* | 8 | 7.0 (4.0–11.2) | 2.18 (50%) | 35.53 (57%) | 26 |

Example 3. Comparative Metabolism Studies of Compound 1 and Compound Z

Metabolism studies of Compound 1 and Compound Z were evaluated in both mouse and dog liver microsome assays. From these studies, Compound 1 was found to be mainly metabolized by CYP3A4 and CYP2C8. Compound 1 was not found to inhibit or induce any major CYP enzymes in the assays. In the mouse liver microscome assay, the major metabolite (>10%) in the mouse plasma was amide bond hydrolysis M2, in addition to minor oxidation metabolites. minor oxidation metabolites were found in the dog plasma evaluated in the dog liver microsome.

In contrast, Compound Z was found to be mainly metabolized by CYP3A4 and CYP3A5. For Compound Z, the major metabolite (>10%) in human plasma is oxidative metabolite M27. Other minor oxidation metabolites were found in both the mouse and dog plasma evaluated.

Example 4. A study of Safety, Tolerability and Efficacy of Compound 1 Alone or in Combination with Other Therapeutic Agents in Patients with Waldenström Macroglobulinemia A clinical study evaluating the safety, tolerability, efficacy and PK of Compound 1 as a single agent or in combination with other therapeutic agents such as ibrutinib or rituximab is conducted. The study consists of dose escalation and dose expansion phases. The clinical trial has multiple arms with the ability to subsequently add more treatment arms based upon clinical activity of Compound 1 in Waldenström Macroglobulinemia (WM). Initially the study contains 3 arms as described below. All arms are independent.

Arm A: Compound 1 is administered as a single agent to determine the MTD/RP2D in the WM patients who are relapsed/resistant or intolerant to ibrutinib or another BTK inhibitor. After the MTD/RP2D is determined, up to 12 additional patients are to be enrolled at the RP2D level in a dose expansion phase to further evaluate safety and efficacy of Compound 1.

Arm B: Compound 1 is administered in combination with ibrutinib in patients with previously untreated WM. MTD/RP2D of Compound 1 in combination with ibrutinib will be established in cycle 1, Arm B. After the MTD/RP2D is determined, up to additional 15 patients will be enrolled at that dose level in a dose-expansion stage.

Arm C: Compound 1 is administered in combination with rituximab in WM patients have relapsed/resistant disease and have never previously been treated with ibrutinib or other BTKi. MTD/RP2D of Compound 1 in combination with rituximab are established in cycle 1 Arm C. After the MTD/RP2D is determined, up to an additional 15 patients are enrolled at that dose level in a dose-expansion stage. Each cycle is 4 weeks (28 days long).

Figure 3:
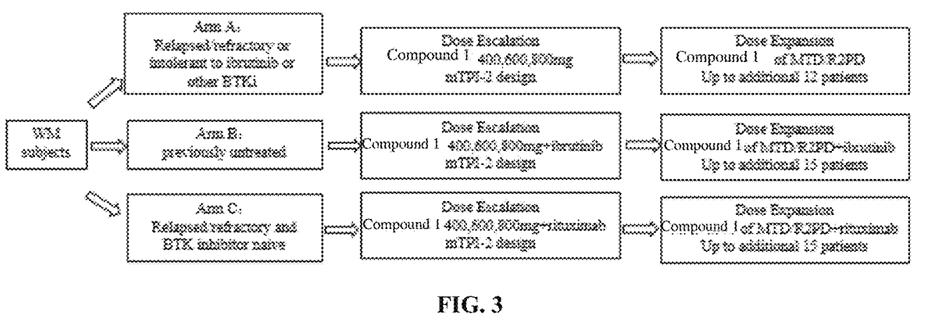
FIG. 3 depicts an exemplary dosing scheme for a Phase Ib/II study of safety, tolerability and efficacy of Compound 1 alone or in combination with other therapeutic agents in patients with Waldenström Macroglobulinemia.

The Dose escalation phase of Compound 1 as monotherapy or in combination with ibrutinib or rituximab will follow mTPI-2 dose escalation design:

Compound 1 is administered orally once daily for consecutive 28 days in a 28-day cycle, until time of progression or unacceptable toxicity. The starting target dose (using ramp-up if needed) is 400 mg (dose level 1; DL1) and is increased to 600 mg (DL2), and 800 mg (DL3) accordingly. Doses can be increased to higher level depending on safety and PK results based on discussions of the Investigators and Sponsor. Ibrutinib will be administered orally at 420 mg, daily beginning from cycle 1 day 1 and continuously thereafter. Each cycle is 4 weeks (28 days). Rituximab is dosed at 375 mg/m² IV per package insert weekly for four consecutive weeks, followed by a second four-week rituximab course after a three-month interval (Day 1 of Weeks 1-4 and Weeks 17-20, total of 8 infusions of rituximab). Rituximab infusion starts from cycle 1 day 1. A dosing schema representing the study is provided in FIG. 3.

All patients are evaluated for their specific risks of tumor lysis syndrome (TLS) and receive prophylaxis (including hydration, anti-hyperuricemics, close laboratory monitoring, and hospitalization if indicated) starting at least 72 hours before the first dose of Compound 1. A ramp-up dosing scheme may be implemented for patients with high risk for TLS regardless of the assigned dose level before reaching the final dose level, for low/intermediate risk TLS patients, they can begin with the final assigned dose. The daily 3-day fixed ramp-up schedule is listed in Table 2 below.

TABLE 2

Compound 1 daily ramp-up schema.

| Dose Level Ramp-up | Day 3 | Day −2 | Day −1 | Day 1 |
|---|---|---|---|---|
| 400 mg | 50 mg | 100 mg | 200 mg | 400 mg* |
| 600 mg | 100 mg | 200 mg | 400 mg | 600 mg** |
| 800 mg | 200 mg | 400 mg | 600 mg | 800 mg*** |

*Cycle 1, Day 1 (C1D1) is the first day at assigned 400 mg dose.
**Cycle 1, Day 1 (C1D1) is the first day at assigned 600 mg dose.
***Cycle 1, Day 1 (C1D1) is the first day at assigned 800 mg dose.

To be considered DLT evaluable, the subject must have received at least 70% of the planned dose of Compound 1 or its combination during DLT evaluation periods (Cycle 1). The patient is not DLT evaluable if he/she discontinues during evaluation periods with total dose received less than 70% of the planned dose for a reason other than DLT. If a subject experiences a DLT (during the DLT assessment period) then treatment with Compound 1 alone or in combination must be interrupted and the patient may be discontinued from the study depending on the severity of the DLT. However, following resolution of the DLT to grade 1 or baseline value, the patient may continue to receive study treatment at a reduced dose level, if appropriate, at the discretion of the investigator.

Example 5. A Clinical Study of Compound 1 as a Single Agent or in Combination with Other Therapeutic Agents in Patients with Relapsed and/or Refractory Chronic Lymphocytic Leukemia (CLL)/Small Lymphocytic Lymphoma (SLL)

Figure 4:
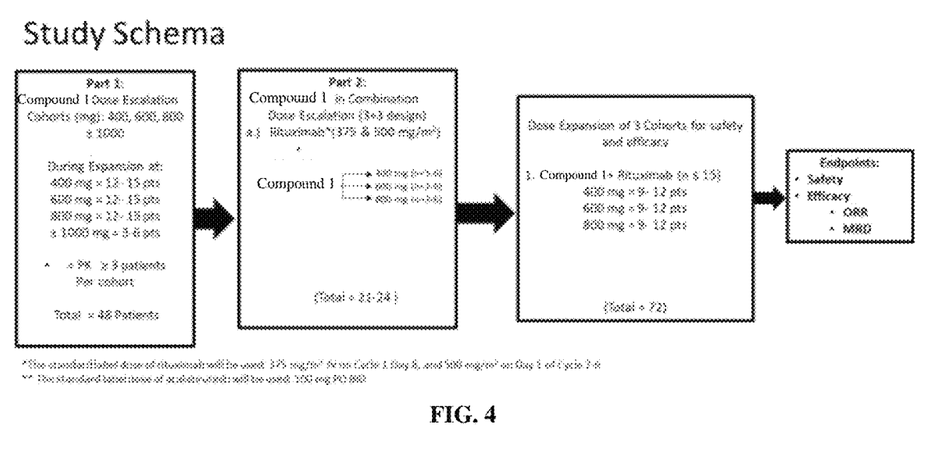
FIG. 4 depicts an exemplary dosing scheme for a Phase Ib/II Study of Compound 1 as a Single Agent or in Combination with Other Therapeutic Agents in Patients with Relapsed and/or Refractory Chronic Lymphocytic Leukemia (CLL)/Small Lymphocytic Lymphoma (SLL).

An open-label study evaluating the safety, tolerability, efficacy and PK of Compound 1 as a single agent or in combination therapy is conducted The study consists of a daily ramp-up period, dose escalation and dose expansion portions. Every patient has gone through a daily ramp-up period prior to enter the treatment cycle. The duration of the daily ramp-up period will depend on the dose level assigned. The daily ramp-up consists of treatment with Compound 1 given once a day starting at 20 mg on Day 1, 50 mg on Day 2, 100 mg on Day 3, 200 mg on Day 4, 400 mg on Day 5, 600 mg on Day 6, 800 mg on Day 7, and 1000 mg on Day 8. Scheduled maximum cohort doses for evaluation start at 400 mg of Compound 1 to a maximum of 1000 mg of Compound 1. For example, patients with a scheduled a dose of 400 mg will have a 4-day ramp-up period, those scheduled at 600 mg, a 5-day ramp-up, etc, see FIG. 1. Part 1 assesses four dose levels (400 mg, 600 mg, 800 mg and 1,000 mg) of Compound 1 monotherapy; Part 2 is a combination of Compound 1 with rituximab and will have a dose escalation and expansion at any safe dose levels including at 400 mg, 600 mg and 800 mg of Compound 1. (see FIG. 4). In this study, the maximum tolerated dose (MTD) is defined as a dose(s) at which of 6 patients treated in the first 28-day cycle is considered not to cause unacceptable toxicities and demonstrated by zero or one patient developing dose limiting toxicities (DLT) where the next higher dose shows unacceptable toxicity ($\geq 2/3$ or $\geq 2/6$ DLTs).

Part 1: Compound 1 is administered orally, once daily (QD) as a single agent to determine the MTD/RP2D in relapsed or refractory CLL patients. Patients will be treated in 28-day cycles. Compound 1 is administered, first through a Daily ramp-up period on Days 1 to 4 (Day 1, 20 mg; Day 2, 50 mg; Day 3, 100 mg; and Day 4, 200 mg) followed by Cycle 1 Day 1 with Compound 1 at 400 mg 600 mg, 800 mg and 1000 mg in parallel. PK analyses are required in the first 3 patients at each dose cohort. At each dose cohort considered to have no safety concerns after first 3 patients, additional patients up to a maximum of 15 may be treated to further characterize safety and efficacy. The optimal dose for Compound 1 monotherapy in CLL are based on the overall safety, PK and preliminary efficacy data following discussion between Investigators and sponsor.

Part 2: Compound 1 is administered in combination with rituximab. Patients are treated in 28-day cycles. Compound 1 starts with a ramp-up on Days 1 to 4 (Day 1, 20 mg; Day 2, 50 mg; Day 3, 100 mg and Day 4, 200 mg) and followed by Cycle 1 Day 1 with Compound 1 at three dose levels, 400 mg, 600 mg, and 800 mg. As stated above, with each higher dose, the ramp-up period increases accordingly. Compound 1 is to be taken until disease progression, unacceptable toxicity, start of alternative therapy or withdrawal of consent. The combination commences on Day 8 of Cycle 1 as follows: Rituximab is administered as 375 mg/m² IV infusion on Day 8 of Cycle 1 and 500 mg/m² IV infusion on Day 1 of Cycles 2-6.

All patients are evaluated for their specific risk of tumor lysis syndrome (TLS) and all will receive prophylaxis (including hydration, anti-hyperuricemic agents, close laboratory monitoring, and hospitalization (if indicated) prior to the first Compound 1 dose. A depiction of the daily Compound 1 ramp-up schedule is detailed in Table 3.

TABLE 3

Compound 1 ramp-up schedule.

| Dose Level | Ramp-up to: | Day 1 (mg) | Day 2 (mg) | Day 3 (mg) | Day 4 (mg) | Day 5 (mg) | Day 6 (mg) | Day 7 (mg) | Day 8 (mg) | Day 9 (mg) |
|---|---|---|---|---|---|---|---|---|---|---|
| 1 | 400 mg | 20 | 50 | 100 | 200 | 400$^a$ | 400 | 400 | 400 | 400 |
| 2 | 600 mg | 20 | 50 | 100 | 200 | 400 | 600$^b$ | 600 | 600 | 600 |
| 3 | 800 mg | 20 | 50 | 100 | 200 | 400 | 600 | 800$^c$ | 800 | 800 |
| 4 | 1000 mg | 20 | 50 | 100 | 200 | 400 | 600 | 800 | 1000$^d$ | 1000 |

Dose Cohorts:
$^a$400 mg, Cycle 1, Day 1;
$^b$600 mg, Cycle 1, Day 1;
$^c$800 mg, Cycle 1, Day 1;
$^d$1000 mg, Cycle 1, Day 1.

Example 6. A Clinical Study of Compound 1 as a Single Agent or in Combination with Chemotherapy for the Treatment of Patients with Relapsed and/or Refractory Acute Myeloid Leukemia (r/r AML)

This is a Compound 1 single-dose escalation study to assess the DLT, MTD, or RP2D of Compound 1 as a single-drug, and to evaluate the in vivo pharmacokinetics and anti-AML efficacy of Compound 1. The dosage of Compound 1 is increased according to the standard 3+3 scheme. The initial dosage cohort of Compound 1 receives 200 mg. The dose is then increased in three dose escalation cohorts with respective dose levels of 400 mg, 600 mg and 800 mg. Compound 1 is administered once daily (QD), and every 28 days is a dosing cycle.

The study follows a Daily Gradient Increasing Dosing Regimen that includes the following. A 200 mg dose group is to be dosed in a daily gradient as follows: 100 mg to 200 mg. A 400 mg dose group is to be dosed in a daily gradient as follows: 100 mg to 200 mg to 400 mg. A 600 mg dose group is to be dosed in a daily gradient as follows: 100 mg to 200 mg to 400 mg to 600 mg. A 800 mg dose group is to be dosed in a daily gradient as follows: 100 mg to 200 mg to 400 mg to 600 mg to 800 mg.

Example 7. Phase Ib/II study of Safety, PK, PD and Efficacy of Compound 1 as a Single Agent or in Combination with Rituximab or Ibrutinib in Patients with Relapsed and/or Refractory Chronic Lymphocytic Leukemia (CLL) or Relapsed and/or Refractory Small Lymphocytic Lymphoma (SLL)

This is an open-label, multi-center Phase Ib/II study of safety, PK, PD, and efficacy of Compound 1 as a single agent or in combination with rituximab or ibrutinib in relapsed and/or refractory CLL and/or SLL patients. Except for Compound 1 and rituximab or ibrutinib, subjects could not accept other anti-malignant tumor research drugs, marketed drugs or treatment methods. Symptomatic supportive treatment is acceptable, including for controlling the symptoms caused by malignant tumors in the subject. A schematic of the study is provided as FIG. 5.

This study consists of two parts. The first part of this study is the Compound 1 single agent expansion cohort study in order to evaluate the safety and antitumor activity and pharmacokinetic profile of Compound 1 monotherapy in patients with relapsed or refractory CLL and/or SLL. The cohort expansion is conducted at three dose levels of 400 mg, 600 mg, and 800 mg, and 12-15 patients are planned to be enrolled into each dose level.

In order to minimize the risk of tumor lysis syndrome (TLS) in subjects in the first part of the study, all subjects receive Compound 1 according to a daily ramp-up scheme before receiving the target dose level treatment. Subjects in the 400 mg dose level cohort receive Compound 1 at consecutive daily doses of 20 mg, 50 mg, 100 mg, 200 mg, and 400 mg, with 400 mg as the target dose. Subjects in the 600 mg dose level cohort receive Compound 1 at consecutive daily doses of 20 mg, 50 mg, 100 mg, 200 mg, 400 mg, and 600 mg, with 600 mg as the target dose. Subjects in the 800 mg dose level cohort receive Compound 1 at consecutive daily doses of 20 mg, 50 mg, 100 mg, 200 mg, 400 mg, 600 mg, and 800 mg, with 800 mg as the target dose.

Figures 5, 5B:
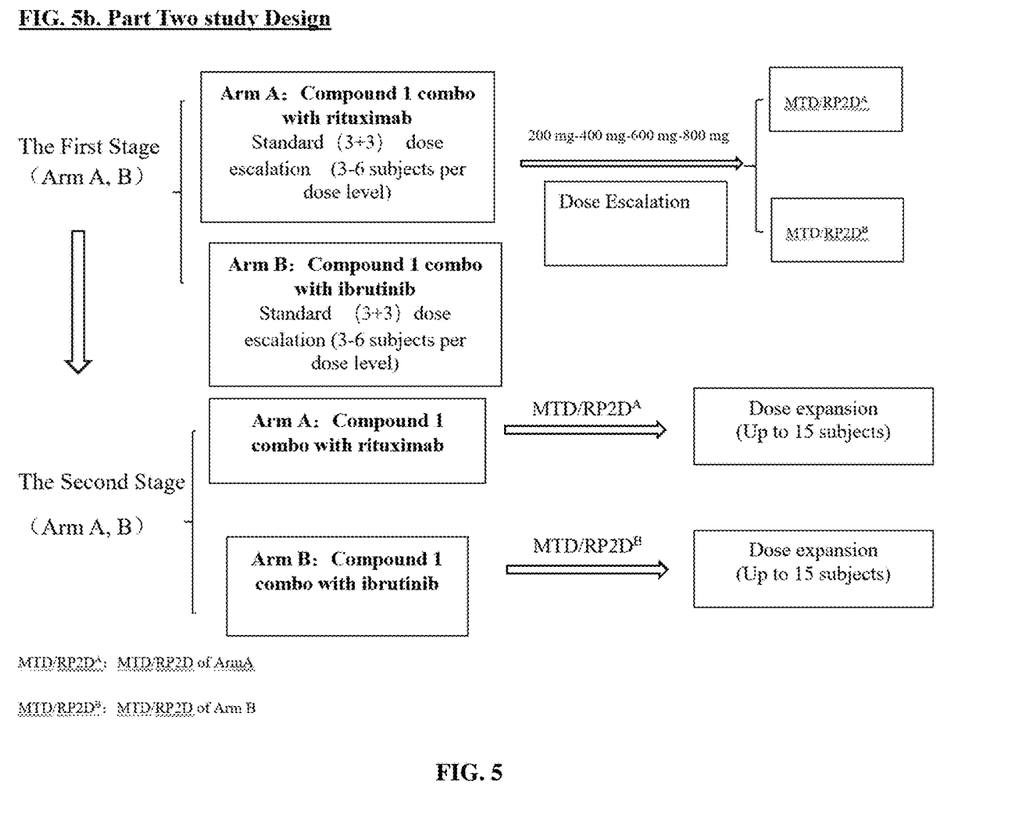
Figure 5A:
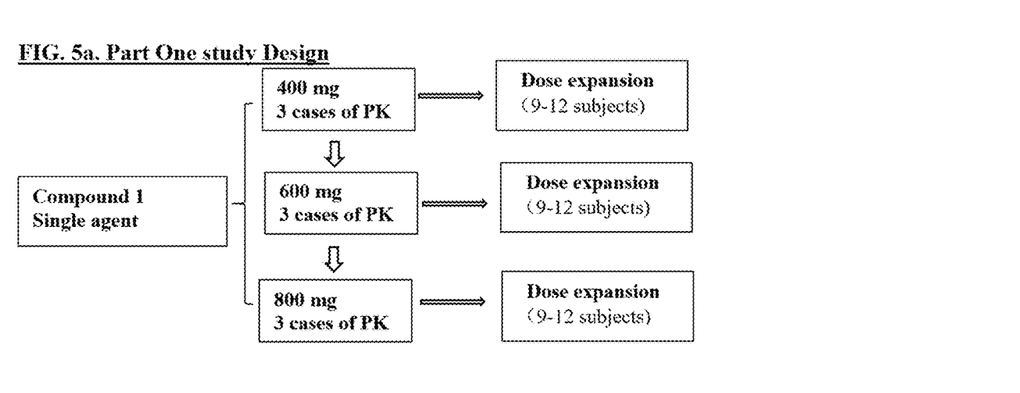

A schematic of the first part of the study is provided in FIG. 5a. The samples of first three subjects in each cohort will be collected for pharmacokinetic (PK) data analysis. After the first 3 patients in the 400 mg cohort are enrolled, the safety of these 3 patients in the first cycle is evaluated. If the evaluation indicates that the drug is safe, the enrollment of 9-12 patients in the 400 mg cohort and the enrollment of the first 3 patients in the 600 mg cohort follows. If the first three patients at 600 mg complete the first cycle of evaluation to show that the drug is safe, the enrollment of the subsequent 9-12 patients in the 600 mg cohort is performed, and the first three patients in the 800 mg cohort are enrolled at the same time. After the PK and safety assessment of the three patients at 800 mg, the last 9-12 patients in the 800 mg cohort are enrolled. If for any reason complete PK samples of 3 subjects cannot be obtained, they are to be replaced by subsequent subjects enrolled in this cohort until complete PK samples of 3 subjects are collected.

Compound 1 is administered continuously orally, once a day, 28 days as a cycle. When all subjects complete 6 cycles of treatment or discontinued treatment (according to whichever occurs first), a preliminary analysis of safety and efficacy is to be conducted. The study of the second part is carried out after the completion of the first part group enrollment.

The second part contains two arms: Compound 1 in combination with rituximab (Arm A) and Compound 1 in combination with ibrutinib (Arm B) (FIG. 5b). The purpose is to explore the DLT, MTD, RP2D, and safety of Compound 1 in the studied combination therapy regimens, as well as pharmacokinetic studies and efficacy evaluation. There are 4 dose levels of Compound 1: 200 mg, 400 mg, 600 mg, and 800 mg. Both the two arms consist of two stages of dose escalation (first stage) and dose expansion (second stage). Subjects of the two arms receive treatment in 28-day cycles. Compound 1 is provided in an oral tablet, with each tablet containing 10 mg or 50 mg of Compound 1.

In order to minimize the risk of tumor lysis syndrome (TLS) in subjects in the second part of the study, all subjects receive Compound 1 according to a daily ramp-up scheme before receiving the target dose level treatment. Subjects in the 200 mg dose level cohort receive Compound 1 at consecutive daily doses of 20 mg, 50 mg, 100 mg, and 200 mg, with 200 mg as the target dose. Subjects in the 400 mg dose level cohort receive Compound 1 at consecutive daily doses of 20 mg, 50 mg, 100 mg, 200 mg, and 400 mg, with 400 mg as the target dose. Subjects in the 600 mg dose level cohort receive Compound 1 at consecutive daily doses of 20 mg, 50 mg, 100 mg, 200 mg, 400 mg, and 600 mg, with 600 mg as the target dose. Subjects in the 800 mg dose level cohort receive Compound 1 at consecutive daily doses of 20 mg, 50 mg, 100 mg, 200 mg, 400 mg, 600 mg, and 800 mg, with 800 mg as the target dose.

The first stage of the second part was a study of Compound 1 dose escalation in combination with rituximab or ibrutinib. Dose escalation of Compound 1 follows a standard 3+3 regimen, with the initial dose being 200 mg and subsequent doses increased, for a total of 4 dose levels (200 mg, 400 mg, 600 mg, and 800 mg). Upon reaching the target dose level after the daily ramp-up scheme, Compound 1 is administered continuously orally, once a day, during 28-day cycles (FIG. 5b).

In the first cycle of the rituximab arm (Arm A), the use of rituximab or ibrutinib starts on Cycle 1, Day 8. Rituximab is infused intravenously on Cycle 1, Day 8 at 375 mg/m$^2$, and on Day 1 of each of Cycles 2-6 at 500 mg/m$^2$, for a total of six infusions per subject.

In the ibrutinib arm, ibrutinib is administered continuously orally at a dose of 420 mg once a day beginning from Cycle 1, Day 8 and continuously thereafter. During the period combination agents were administered in each respective treatment arm, rituximab is administered within 30-90 minutes after oral administration of Compound 1, and Compound 1 and ibrutinib are administered simultaneously.

The second stage of the second part of the study is the RP2D expansion stage. Once the respective RP2D of Arms A and B is determined, each arm enters the expansion cohort of the second stage of the study (FIG. 5b). Up to 15 subjects in each RP2D dose level receive Compound 1 combined with rituximab or ibrutinib to further evaluate the safety and efficacy of the combined regimen at this dose level. Both Arms A and B allow for the subject's own dose to escalate. Before the investigator and the sponsor make their intra-patient dose escalation, the subject needs to complete at least 3 cycles of dosing at the originally assigned dose level and the safety of the higher dose level is be determined. Subjects with their intra-patient dose escalation take the current dose as the starting dose of the gradient escalation, daily ramp up, reach the target dose to complete the gradual escalation, and take the reach target dose day as the Day 1 of the medication cycle. From the day before administration of Compound 1, the patient is hospitalized until at least 48 hours after reaching the target dose, and received intravenous hydration every day while closely monitoring and timely handling with any metabolic changes suggesting tumor lysis.

Example 8. A Phase Ib/II Clinical Study of Compound 1 in Combination with Pd or DRd for the Treatment of Patients with Relapsed and/or Refractory Multiple Myeloma (RRMM)

Figure 6:
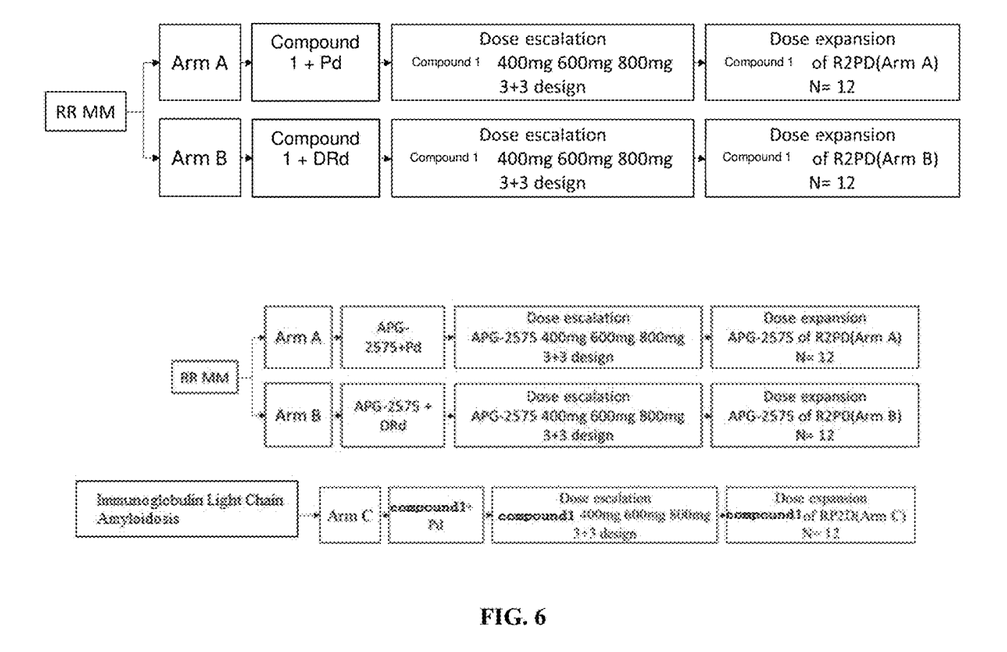
FIG. 6 depicts a study design for an exemplary Phase Ib/II clinical study of Compound 1 in combination with Pd or DRd for the treatment of patients with relapsed and/or refractory multiple myeloma (RRMM). The study contains a treatment arm for dose-escalation and dose-expansion studies of Compound 1 in combination with Pd and another treatment arm for dose-escalation and dose-expansion studies of Compound 1 in combination with DRd.

This is a Phase Ib/II, open-label, multi-center study evaluating the safety, tolerability, efficacy, and PK/PD studies of Compound 1 in combination with Pd (combination of pomalidomide and dexamethasone) or DRd (combination of daratumumab, lenalidomide, and dexamethasone) in patients with relapsed/refractory (RR) multiple myeloma (MM). The study consists of dose escalation and dose expansion phases. The study starts with 2 arms noted below, and both arms are independent. A scheme of the study design is provided as FIG. 6 and is further described below.

In this protocol, study treatment is defined as pomalidomide (P), dexamethasone (d) and Compound 1 in Arm A, and daratumumab (D), lenalidomide (R), dexamethasone (d), and Compound 1 in Arm B. The study drug is Compound 1. Subjects whose Pd or DRd treatment is discontinued may continue to receive Compound 1 during the course of the study.

All patients receive tumor lysis syndrome (TLS) prophylaxis (including hydration, anti-hyperuricemias, close laboratory monitoring, and hospitalization if indicated) starting at least 72 hours before the first Compound 1 dose. In case any TLS in a clinical or laboratory setting occurs during the dose escalation phase of Arm A or Arm B, the protocol may be modified to implement a daily ramp-up dosing scheme of Compound 1 in subsequent patients enrolled.

Arm A: Compound 1 is administered in combination with Pd to determine the MTD/RP2D in subjects with RRMM. Patients receive Compound 1 at the target dose level once daily in combination with pomalidomide (4 mg) on Days 1 through 21 and dexamethasone (40 mg, or 20 mg for patients greater than 75 years old) on Days 1, 8, 15, and 22 of a repeated 28-day cycle. Patients may continue to receive treatment until disease progression, unacceptable toxicity, withdrawal of consent or proceed to stem cell transplantation, whichever comes first. Dose modifications may be made based on toxicities/age. This is an all-oral regimen.

A 3+3 dose escalation design is utilized in the dose escalation phase of Compound 1 in combination with Pd. The starting target dose of Compound 1 is 400 mg once daily (dose level 1, or DL1) and is escalated in subsequent cohorts to 600 mg once daily (dose level 2, or DL2) and 800 mg once daily (dose level 3, or DL3) accordingly. Dose reduction to 200 mg once daily (dose level-1, or DL-1) is acceptable if Compound 1 at a dose of 400 mg cannot be tolerated. This rule-based design first proceeds with a cohort of three patients at DL1. If none of the three patients enrolled at DL1 experiences a DLT, another three patients will be treated at DL2, and so on. However, if one patient experiences a DLT, three more patients will be treated at the same dose level. The dose escalation continues until at least two patients among a cohort of three to six patients experience DLT. MTD is conventionally defined as the highest dose level at which ≤33% of patients experience DLT. Higher dose levels beyond 800 mg are considered after a comprehensive analysis of safety data to determine whether a 800 mg dose can be tolerated. The RP2D of Arm A is determined based on efficacy and safety profile of Compound 1.

After the MTD and RP2D of Arm A are determined, up to 12 additional patients are enrolled at the RP2D (Arm A) in a dose-expansion phase to further evaluate the safety and efficacy of Compound 1 in combination with Pd.

Arm B: Compound 1 is administered in combination with DRd to determine the Arm B MTD and RP2D in RRMM subjects. Arm B is not to be opened until the 600 mg dose level of Arm A is determined to be safe. Both arms is then simultaneously recruit patients based on the investigator's discretion.

Patients receive Compound 1 at target dose once daily in 28-day cycles, beginning from Cycle 1 day 1 onwards. For the backbone therapy, patients receive lenalidomide administered at a dose of 25 mg orally (PO) once daily on Days 1 through 21 of each 28-day cycle, dexamethasone will be administered at a dose of 40 mg (or 20 mg for patients greater than 75 years old) once weekly, and daratumumab will be administered intravenously at a dose of 16 mg/kg (or 1800 mg administered subcutaneously if commercially available) weekly in cycles 1 and 2 and then every 2 weeks in cycles 3 to 6 and every 4 weeks thereafter. Patients may continue to receive treatment until disease progression, unacceptable toxicity, withdrawal of consent or proceed to stem cell transplantation, whichever comes first. Dose modifications may be made based on toxicities/age.

Compound 1 in combination with DRd follows a 3+3 dose escalation design. The starting target dose is 400 mg once daily (dose level 1, or DL1) and is increased in subsequent cohorts to 600 mg once daily (dose level 2, or DL2) and 800 mg once daily (dose level 3, or DL3) accordingly. Dose reduction to 200 mg (dose level-1, or DL-1) is acceptable if Compound 1 at a dose of 400 mg cannot be tolerated. This rule-based design first proceeds with a cohort of three patients at DL1. If none of the three patients enrolled at DL1 experiences a DLT, another three patients will be treated at DL2, and so on. However, if one of three patients experiences a DLT, three more patients will be treated at the same dose level. The dose escalation continues until at least two patients among a cohort of three to six patients experience DLT. MTD is conventionally defined as the highest dose level at which ≤33% of patients experience DLT. Higher dose levels beyond 800 mg will be considered only after a comprehensive analysis of safety data to determine whether a 800 mg dose can be tolerated. The RP2D of Arm B is determined based on efficacy and safety profile of Compound 1.

After the MTD and RP2D of Arm B are determined, up to 12 additional patients will be enrolled at the Arm B RP2D in a dose-expansion phase to further evaluate safety and efficacy of Compound 1 in combination with DRd.

In either Arm A or Arm B, patients who are not evaluable for DLT assessment during Cycle 1 and/or withdrawn during the defined DLT assessment treatment cycle for any reason other than a DLT, and/or does not receive more than 70% planned dose in one cycle (Compound 1 and/or the combinational investigational drugs) is considered as non-evaluable and be replaced. Stable or responding patients who experience DLTs may continue on therapy once DLTs have resolved to less than or equal to Grade 1 base on the discussion between the investigator and Ascentage medical monitor.

A Phase Ib/II Open-Label Study of COMPOUND 1 in Combination with Novel Therapeutic Regimens in Subjects with Relapsed or Refractory Multiple Myeloma and Immunoglobulin Light Chain Amyloidosis Arm C: COMPOUND 1 will be administered in combination with Pd to determine the MTD and RP2D of COMPOUND 1 in subjects with AL amyloidosis.

Patients will receive COMPOUND 1 once daily for 28 days plus pomalidomide (4 mg) on Days 1 through 21 and dexamethasone (40 mg for patients ≤75 years old or 20 mg for patients >75 years old) on Days 1, 8, 15, and 22 of a repeated 28-day cycle. Patients may continue to receive treatment until disease progression, unacceptable toxicity, withdrawal of consent or proceed to stem cell transplantation, whichever comes first. Dose modifications may be made based on toxicities/age. This is an all-oral regimen.

Example 9. A Phase Ib/II Open-Label Study of Compound 1 Monotherapy or in Combination with Lenalidomide/Dexamethasone in Subjects with Relapsed and/or Refractory Multiple Myeloma This is a Phase Ib/II, open-label, multi-center study evaluating the safety, tolerability, efficacy, and Pharmacokinetics/Pharmacodynamics of Compound 1 monotherapy or in combination with Rd (combination of lenalidomide (R) and dexamethasone (d)) in patients with relapsed and/or refractory (R/R) multiple myeloma (MM). The primary objective is to evaluate the safety and tolerability, identify dose-limiting toxicities (DLT), the maximum tolerated dose (MTD) and the recommended dose (RP2D) of Compound 1 monotherapy or in combination with Rd in Chinese R/R MM patients.

Figure 7:
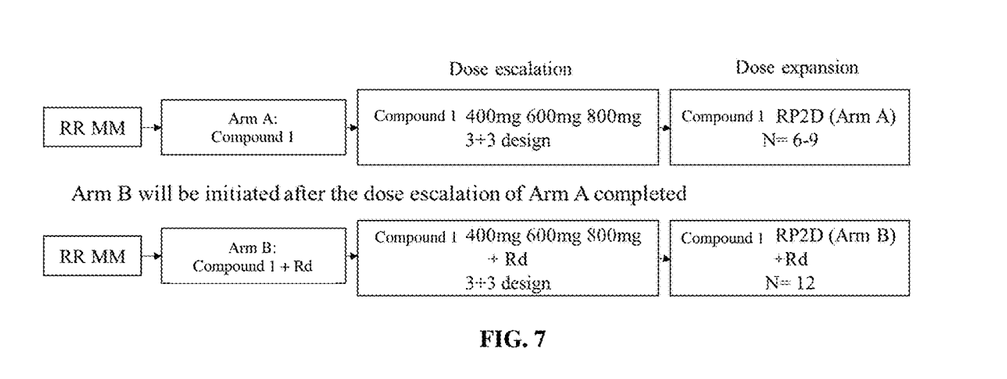
FIG. 7 depicts a study design for an exemplary Phase Ib/II clinical study of Compound 1 as a monotherapy or in combination with Rd for the treatment of patients with relapsed and/or refractory multiple myeloma. The study contains a treatment arm for dose-escalation and dose-expansion studies of Compound 1 monotherapy and another treatment arm for dose-escalation and dose-expansion studies of Compound 1 in combination with Rd.

This study consists of two arms of Compound 1 single agent (Arm A) and Compound 1 in combination with Rd (Arm B). Both arms include dose escalation and dose expansion phases. Arm B is initiated after the dose escalation phase of Arm A completed. The starting dose and maximum escalation dose of Compound 1 in Arm B may be adjusted based on the MTD/RP2D of Compound 1 in Arm A. All subjects receive consecutive treatment in 28-day cycles. The study is summarized below as well as depicted in FIG. 7.

In Arm A, Compound 1 is administered once daily in 28-day cycles. In Arm B, Compound 1 is be administered once daily in 28-day cycles. Patients receive lenalidomide administered at a dose of 25 mg (or 10 mg for patients with a rate of creatinine clearance (CrCl) of 30-60 mL/min) orally (PO) on Days 1 through 21 of each 28-day cycle. Dexamethasone is administered at a dose of 40 mg (or 20 mg for patients >75 years old) once weekly (Days 1, 8, 15, and 22).

A 3+3 design is utilized in dose escalation phase of Compound 1 monotherapy in Arm A and Compound 1 in combination with Rd in Arm B. The starting target dose of Compound 1 is 400 mg (dose level 1, or DL1) and is escalated subsequently to 600 mg (dose level 2, or DL2) and 800 mg (dose level 3, or DL3) accordingly. This rule-based design first proceeds with cohorts of three patients. If none of the 3 patients enrolled in DL1 experiences a DLT, 3 other patients will be treated at DL2, and so on. However, if 1 patient experiences a DLT, 3 more patients will be treated at the same dose level. Dose escalation continues until at least 2 patients at the same cohort of 3 to 6 patients experience DLT. The MTD is conventionally defined as the highest dose level at which ≤33% of patients experience a DLT. The RP2D is determined based on overall efficacy and safety profile of Compound 1 monotherapy or in combination with Rd. After the RP2D is determined, 6-9 additional patients in Arm A and up to 12 additional patients in Arm B will be enrolled at the RP2D in dose-expansion phase to further evaluate safety and efficacy of Compound 1 monotherapy or in combination with Rd respectively.

To minimize tumor lysis syndrome (TLS) risk, all patients in dose escalation phase receive a 3-day monitoring (TLS chemistry and complete blood cell test) prior to and after their first Compound 1 dose. If no TLS (clinical or laboratory) is noted during dose escalation, TLS monitoring on Days 2 and 3 are no longer needed for patients in dose expansion unless required by investigator.

All subjects continue to receive treatment until disease progression, unacceptable toxicities, or other treatment discontinuation criteria defined by the protocol. All subjects are to complete survival follow up after treatment discontinuation until end of the study, withdrawal of informed consent, loss of follow-up, or death.

Example 10. A Phase Ib Study of Compound 1 Monotherapy and in Combination with Homoharringtonine (HHT) or Azacytidine (AZA) in Relapsed and/or Refractory Acute Myeloid Leukemia (r/r AML) Patients This is a Phase Ib open-label, dose escalation study of Compound 1 monotherapy and Compound 1 in combination with HHT or AZA in the treatment of relapsed and refractory acute myeloid leukemia (AML). With the exception of Compound 1, HHT, and AZA, subjects cannot receive other anti-malignant tumor research drugs, marketed drugs, or treatments. Patients may receive symptomatic supportive treatment, including for controlling symptoms caused by the subject's malignant tumor. This study consists of three stages.

First Stage—Dose Escalation of Compound 1 Monotherapy

The first stage is a Compound 1 monotherapy dose escalation study, the purpose of which is to explore the DLT, MTD, and/or RP2D of Compound 1 monotherapy, and to evaluate the pharmacokinetics and anti-AML efficacy of Compound 1. The dose of Compound 1 is escalated in dose level cohorts according to a standard 3+3 design. The initial dose is 200 mg, which is sequentially escalated to 400 mg, 600 mg, and 800 mg. Compound 1 is administered orally once daily (QD) at the target dose level studied, and all subjects receive consecutive treatment of the target dose levels in 28-day cycles.

In order to minimize the risk of clinical or laboratory tumor lysis syndrome (TLS) in the first stage, all subjects received daily ramp-up regimens up to each dose level as follows. Subjects in the 200 mg dose level cohort receive Compound 1 at consecutive daily doses of 100 mg, and 200 mg, with 200 mg as the target dose. Subjects in the 400 mg dose level cohort receive Compound 1 at consecutive daily doses of 100 mg, 200 mg, and 400 mg, with 400 mg as the target dose. Subjects in the 600 mg dose level cohort receive Compound 1 at consecutive daily doses of 100 mg, 200 mg, 400 mg, and 600 mg, with 600 mg as the target dose. Subjects in the 800 mg dose level cohort receive Compound 1 at consecutive daily doses of 100 mg, 200 mg, 400 mg, 600 mg, and 800 mg, with 800 mg as the target dose. See Table 4.

TABLE 4

Dose escalation design of the first stage.

| Dose level | Designated dose of Compound 1 | Initial dose | Days to reach the designated dose (Cycle 1 Day 1) |
|---|---|---|---|
| 1 | 200 mg | 100 mg | the second day |
| 2 | 400 mg | 100 mg | the third day |
| 3 | 600 mg | 100 mg | the fourth day |
| 4 | 800 mg | 100 mg | the fifth day |

Second Stage—Dose Escalation of Compound 1 in Combination Regimens

The second stage is the dose-escalation study of Compound 1 in combination with HHT or AZA. The purpose of this second stage is to determine the DLT, MTD or RP2D of Compound 1 and HHT or AZA combination therapy, and to evaluate the pharmacokinetics and anti-AML efficacy of Compound 1 in these combination regimens. Compound 1 dose-escalation in the combination studies follows a standard 3+3 design, and the dose levels studied are the MTD/RP2D-1 of the first stage (i.e., one dose level lower than the MTD/RP2D of the first stage) and the MTD/RP2D level of the first stage, for a total of two dose levels in three combination regimens studied. Compound 1 is orally administrated at each dose level once a day (QD) in 28-day cycles.

In order to minimize the risk of clinical or laboratory tumor lysis syndrome (TLS) in the second stage, all subjects first receive daily ramp-up regimens up to each dose level as follows. Subjects in the RP2D-1 dose level cohort receive Compound 1 beginning at 100 mg, which is then administered, consecutively, in 100 mg daily increases until the RP2D-1 is reached as the target dose. Subjects in the RP2D dose level cohort receive Compound 1 beginning at 100 mg, which is then administered, consecutively, in 100 mg daily increases until the RP2D is reached as the target dose. See Table 5.

TABLE 5

Dose escalation design of the second stage.

| Dose level | Designated dose of Compound 1 | Initial dose | | Days to reach the designated dose (Cycle 1 Day 1) |
|---|---|---|---|---|
| 1 | MTD/RP2D-1 | 100 | mg | the n-1$^{th}$ day* |
| 2 | MTD/RP2D | 100 | mg | the n$^{th}$ day* |

*n = 2-5

Subjects who receive the initial dose on the first day, if tolerated, are given a daily ramp-up according to the above-mentioned regimens based on the designated dose level. The initial dose of the daily ramp-up administration is fixed at 100 mg, and Cycle 1 Day 1 of the medication cycle is reached on the day when the designated dose is reached.

Subjects continue to receive treatment until disease progression, intolerable toxicity, or transfer to other appropriate treatments or when the investigator believes that they cannot benefit or meet other criteria for terminating treatment as designated in the protocol. Regardless of whether the treatment is terminated or not, subjects will be followed up for survival (except for withdrawal of informed consent or loss of follow-up).

The initial dose and dose escalation of the Compound 1 combination regimen will be discussed and decided by the sponsor and the investigator based on the clinical results and PK data of monotherapy dose exploration, and with appropriate dose adjustments.

The combination regimens of these two dose levels are each studied in 3 cohorts. Cohort A of each dose level receives Compound 1 in combination with a reduced-dose HHT treatment. The HHT usage is 1 mg once a day by intravenous infusion for 14 consecutive days, for a total of 14 infusions. Cohort B of each dose level is treated with Compound 1 in combination with standard-dose HHT. In Cohort B, the usage of HHT is 2 mg/m$^2$ by intravenous infusion, once a day for 7 consecutive days, for a total of 7 infusions. HHT is administered as an intravenous infusion for 4 hours, which is administered in combination with orally administered Compound 1 within an interval of not more than 30 minutes from initial administration of HHT. Cohort C of each dose level receives Compound 1 in combination with AZA. AZA is administered subcutaneously at a dose of 75 mg/m$^2$ once a day for 7 consecutive days. AZA is concurrently administered with orally administered Compound 1 within an interval not exceeding 30 min from initial administration of AZA.

The sponsor decides the RP2D dose of Compound 1 in each the combination regimen based on clinical data. Once the RP2D of Compound 1 in each combination regimen is determined, the study will proceed to a third stage, which is the expansion study of the combination regimen.

Third Stage—Expansion Study

The expansion study consists of 3 cohorts. Up to 15 patients with relapsed and refractory AML receive Compound 1 in combination with HHT or AZA at the RP2D dose level in each combination cohort as determined from the second stage. Cohort A receives Compound 1 in combination with a reduced-dose HHT treatment. The HHT usage is 1 mg once a day by intravenous infusion for 14 consecutive days, for a total of 14 infusions. Cohort B is treated with Compound 1 in combination with standard-dose HHT. In Cohort B, the usage of HHT is 2 mg/m$^2$ by intravenous infusion, once a day for 7 consecutive days, for a total of 7 infusions. HHT is administered as an intravenous infusion for 4 hours, which is administered in combination with orally administered Compound 1 within an interval of not more than 30 minutes from initial administration of HHT. Cohort C receives Compound 1 in combination with AZA. AZA is administered subcutaneously at a dose of 75 mg/m$^2$ once a day for 7 consecutive days. AZA is concurrently administered with orally administered Compound 1 within an interval not exceeding 30 min from initial administration of AZA.

The third stage further evaluates the safety and efficacy of the combination regimens at this dose level in patients with relapsed and refractory AML.

In order to minimize the risk of clinical or laboratory tumor lysis syndrome (TLS) in the third stage, all subjects first receive daily ramp-up regimens up to each dose level as follows. Subjects in the RP2D (second stage) dose level cohort receive Compound 1 beginning at 100 mg, which is then administered, consecutively, in 100 mg daily increases until the RP2D is reached as the target dose. See Table 6.

TABLE 6

Dose escalation design of the third stage.

| Dose level | Designated dose of | Initial dose Compound 1 | Days to reach the designated dose (Cycle 1 Day 1) |
|---|---|---|---|
| 1 | MTD/RP2D | 100 mg | the n$^{th}$ day* |

*n = 2-5

Equivalents

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of treating a hematologic malignancy in a patient in need thereof, comprising:
   administering a daily step-wise dosing regimen of a compound(S)-N-((4-(((1,4-dioxan-2-yl) methyl) amino)-3-nitrophenyl) sulfonyl)-2-((1H-pyrrolo [2,3-b]pyridin-5-yl) oxy)-4-(4-((6-(4-chlorophenyl) spiro [3.5] non-6-en-7-yl) methyl) piperazin-1-yl) benzamide or a pharmaceutically acceptable salt thereof;
   wherein administering the daily step-wise dosing regimen comprises:
   administering a first dose of 20 mg of the compound to the patient for one day;
   administering a second dose of 50 mg of the compound to the patient for one day, on the day after the first dose, and
   administering a third dose of 100 mg of the compound to the patient for one day, on the day after the second dose
   wherein the patient has a reduced risk of tumor lysis syndrome during administration of the daily step-wise dosing regimen.

2. The method of claim 1, further comprising administering to the patient a fourth dose of 200 mg of the compound daily for 1 to 5 days or more.

3. The method of claim 2, wherein the daily step-wise regimen further comprises administering to the patient a fifth dose of 400 mg after the fourth dose is administered.

4. The method of claim 3, further comprising administering to the patient a daily dose of 400 mg, 600 mg, 800 mg, or 1000 mg of the compound for 1 week or more, or 1 month or more, after administering the daily step-wise dosing regimen.

5. The method of claim 1, wherein the hematologic malignancy is selected from the group consisting of chronic lymphocytic leukemia, acute myeloid leukemia, multiple myeloma, lymphoplasmacytic lymphoma, non-Hodgkin's lymphoma, small lymphocytic leukemia, Waldenström Macroglobulinemia, and Immunoglobulin Light Chain Amyloidosis.

6. The method of claim 1, further comprising administering to the patient a member of the group consisting of: rituximab, azacytidine, decitabine, low-dose cytarabine, a BTK inhibitor, topetecan, an MDM2 inhibitor, a CD20 inhibitor, a CDK9i inhibitor, or Homoharringtonine (HTT) inhibitor before, during or after the daily step-wise dosing regimen.

7. A method of treating a hematologic malignancy in a patient in need thereof, comprising:
   administering a daily step-wise dosing regimen of a compound(S)-N-((4-(((1,4-dioxan-2-yl) methyl) amino)-3-nitrophenyl) sulfonyl)-2-((1H-pyrrolo [2,3-b]pyridin-5-yl) oxy)-4-(4-((6-(4-chlorophenyl) spiro [3.5] non-6-en-7-yl) methyl) piperazin-1-yl) benzamide or a pharmaceutically acceptable salt thereof;
   wherein administering the daily step-wise dosing regimen comprises
   administering a first dose of 20 mg to 100 mg of the compound to the patient for one day;
   administering a second dose of 50 mg to 200 mg of the compound to the patient for one day, on the day after the first dose
   wherein the patient, during or after administration of the daily step-wise dosing regimen, has a reduced risk of tumor lysis syndrome.

8. The method of claim 7, wherein the daily step-wise dosing regimen further comprises administering a third dose of 100 to 400 mg of the compound to the patient for one day, on the day after the second dose.

9. The method of claim 8, wherein the daily step-wise dosing regimen further comprises administering a fourth dose of 200 mg to 800 mg of the compound to the patient for one to seven days after the third dose.

10. The method of claim 9, further comprising administering to the patient, after the daily step-wise dosing regimen, about 400 mg to 1000 mg of the compound daily for 1 week or more.

11. The method of claim 7, wherein the hematologic malignancy is selected from the group consisting of chronic lymphocytic leukemia, acute myeloid leukemia, multiple myeloma, lymphoplasmacytic lymphoma, non-Hodgkin's lymphoma, small lymphocytic leukemia, Waldenström Macroglobulinemia, and Immunoglobulin Light Chain Amyloidosis.

12. The method of claim 7, further comprising administering to the patient a member of the group consisting of rituximab, azacytidine, decitabine, low-dose cytarabine, a BTK inhibitor, topetecan, an MDM2 inhibitor, a CD20 inhibitor, a CDK9i inhibitor, and Homoharringtonine (HTT) inhibitor, before, during or after the daily step-wise dosing regimen.

* * * * *